United States Patent [19]

Sunago et al.

[11] Patent Number: 4,517,973
[45] Date of Patent: May 21, 1985

[54] LASER SCALPEL

[75] Inventors: Katsuyoshi Sunago; Shinya Takenaka, both of Osaka, Japan

[73] Assignee: Sumitomo Electric Industries, Ltd., Osaka, Japan

[21] Appl. No.: 395,306

[22] Filed: Jul. 6, 1982

[30] Foreign Application Priority Data

Jul. 7, 1981 [JP] Japan .................... 56-100113[U]

[51] Int. Cl.³ ............................................ A61B 17/36
[52] U.S. Cl. ................................ 128/303.1; 128/395
[58] Field of Search .............................. 128/303.1, 395; 248/330.1, 331, 332; 433/107–109

[56] References Cited

U.S. PATENT DOCUMENTS

| 1,026,186 | 5/1912 | Trenaman | 433/109 X |
| 2,810,196 | 10/1957 | Lauterbach | 433/107 X |
| 3,393,889 | 7/1968 | Ogden | 248/331 X |
| 3,528,424 | 9/1970 | Ayres | 128/303.1 |
| 3,821,510 | 6/1974 | Muncheryan | 128/303.1 X |
| 3,913,582 | 10/1975 | Sharon | 128/303.1 |
| 4,069,823 | 1/1978 | Isakov et al. | 128/303.1 |

FOREIGN PATENT DOCUMENTS

| 1022354 | 1/1958 | Fed. Rep. of Germany . |
| 2145526 | 3/1973 | Fed. Rep. of Germany . |
| 2409852 | 9/1975 | Fed. Rep. of Germany ...... 128/395 |
| 2640863 | 9/1976 | Fed. Rep. of Germany ...... 128/395 |
| 2530478 | 5/1977 | Fed. Rep. of Germany . |

Primary Examiner—Edward M. Coven
Attorney, Agent, or Firm—Cushman, Darby and Cushman

[57] ABSTRACT

A laser scalpel in which optical fiber is used as the optical wave guide and the optical fiber is guided from a laser main body housing a laser source therein to the areas to be irradiated along a shore means provided on the laser main body is disclosed. The optical fiber is provided with a hand piece on the exterior of the forward end portion. The hand piece is so constructed that it facilitates the directing of the forward end of the fiber toward the areas to be irradiated. A supporting wire means is provided along the shore means so as to be axially movable. The forward end of the wire means is connected to the hand piece and the rear end of the wire means is connected to a balancing means for counterbalancing at least the weight of said hand piece.

12 Claims, 3 Drawing Figures

LASER SCALPEL

BACKGROUND OF THE INVENTION

The present invention relates to an improvement of a laser scalpel in which optical fibers are used for optical wave guides.

One practical application of laser is as a laser scalpel for use in the medical field, particularly for medical treatments and operations of minute areas requiring high accuracy.

These days, light and flexible optical fibers are frequently used in a laser scalpel instead of the conventional optical wave guides of mirror reflecting type. As shown in FIG. 1, this laser scalpel consists of a laser main body 1 in which a laser oscillating portion as a laser source 17 and the like are housed and a shore 4 consisting of an upright post 2 standing on said laser main body 1 and an arm 3 which is extended horizontally and fixed to said post 2 at one end thereof. An optical fiber 5 is guided along said shore 4 and fixed thereto by means of clasps 6. The forward end of the fiber is hung down from the forward end of said arm 3.

Accordingly, although a laser scalpel is used by directly grasping the forward end of said optical fiber 5 or mounting the forward end of said optical fiber 5 on an endoscope, it is difficult to direct the laser in directions other than the axial direction of the optical fibers and therefore, the laser beam can not be directed correctly and the application of a laser scalpel is limited in dependence upon shapes and positions of the portions to be irradiated. In addition, as the optical fiber 5 is always hung down from the forward end of said arm 3, it gets in the way when the laser scalpel is not being used during an operation.

SUMMARY OF THE INVENTION

An object of the present invention is to provide a laser scalpel in which the disadvantages incidental to the conventional laser scalpel are dissolved, laser irradiation ranges are extended, and optical fibers used as optical wave guides do not get in the way when the laser scalpel is not being used.

Another object of the present invention is to provide a laser scalpel which is simple in construction and easy to handle.

The present invention may be summarized as a laser scalpel in which an optical fiber is used as the optical wave guide and the optical fiber is guided from a laser main body housing a laser source therein to the areas to be irradiated along a shore means provided on the laser main body. The optical fiber is provided with a hand piece on the exterior of the forward end portion. The hand piece is so constructed that it facilitates the orientation of the forward end of the fiber toward the areas to be irradiated. A supporting wire is provided along the shore so as to be axially movable. The forward end of the wire is connected to the hand piece and the rear end of the wire is connected to a balancing means for at least counterbalancing the weight of the hand piece.

DESCRIPTION OF THE PREFERRED EMBODIMENTS

A preferred embodiment of a laser scalpel according to the present invention will be described below in detail by reference to the drawings.

Figure 1:
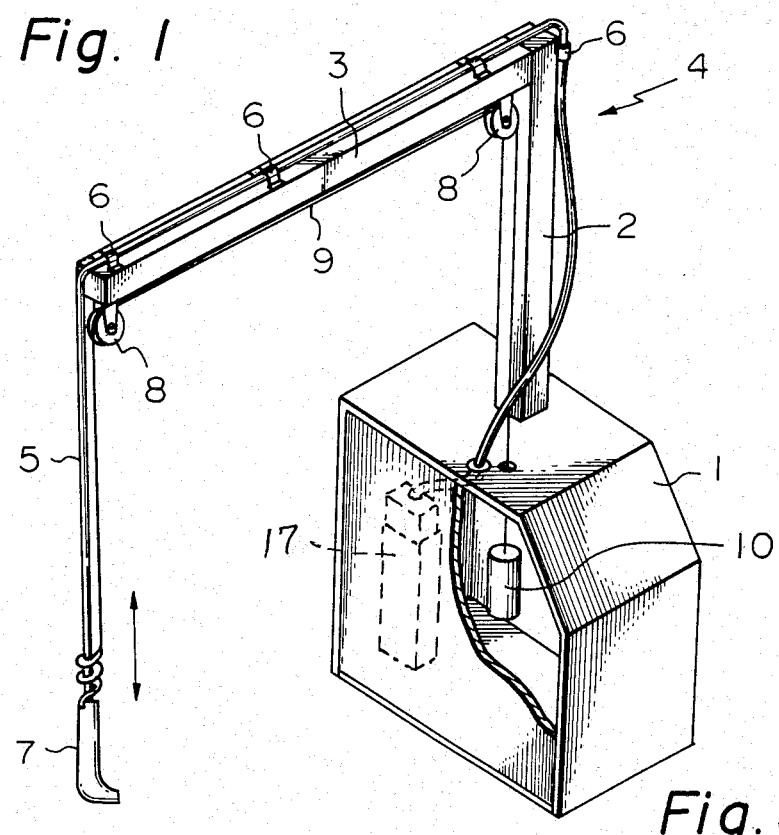
FIG. 1 is a partly cut out perspective view showing a preferred embodiment of a laser scalpel unit according to the present invention.

FIG. 1 is a perspective view showing a preferred embodiment of a laser scalpel according to the present invention.

Figure 2:
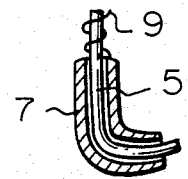
FIG. 2 is a longitudinal cross section of a hand piece.

As described above, an optical fiber 5, which is used for an optical wave guide, is guided along and is fixed on a shore 4, which consists of an upright post 2 standing on a laser main body 1 housing a laser 17 and a horizontal arm 3, by means of clasps 6. The forward portion of the fiber 5 is hung down from the forward end of said arm 3. A hand piece 7 adapted to be grasped by an operator's hand is provided on the forward end of said optical fiber 5. The hand piece 7 is fixed to the coating of said optical fiber 5 by means of adhesives and the like as shown in FIG. 2. The hand piece 7 has an inside diameter slightly larger than the outside diameter of said optical fiber 5 and can be constructed in various shapes so that the forward end thereof may be easily directed to the areas to be irradiated, for example in the shape of letter L. The application of the hand piece 7 having various shapes makes it possible to easily direct the laser beam on the areas which can not be irradiated by the conventional laser scalpel units.

On the other hand, blocks 8 are mounted on the lower surface of both end portions of said arm 3 and a wire 9 is passed through the blocks 8 and is installed along said optical fiber 5 so as to be slidable in the axial direction. The forward end of said wire 9 is fixedly connected to the rear end of said hand piece 7 and the rear end portion of said wire 9 is inserted into said main body 1 of a laser scalpel and is connected with a weight 10 acting as a balancing means for supporting the combined weight of the hanging down portion of said optical fiber 5 and said hand piece 7.

Accordingly, the weight acting on the hanging portion of said optical fiber 5 and the like is supported through said wire 9 and counter-balanced by said weight 10 and thereby said hand piece 7 can be held at the desired position by moving said wire 9 through said blocks 8 while said hand piece 7 can be positioned above when the laser scalpel unit is not being used.

By this, breakage of the optical fiber 5 due to the weight of the hand piece 7 and the hanging portion of the fiber is prevented. Also, the hand piece 7 and the fiber 5 do not get in the way when the unit is not being used.

Figure 3:
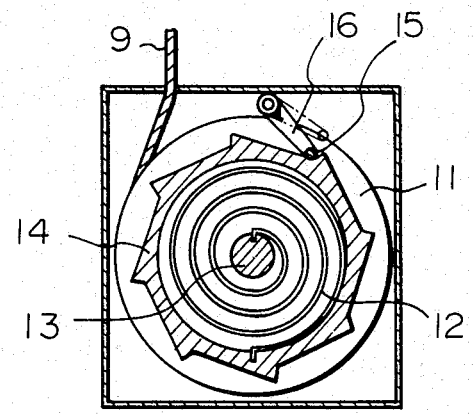
FIG. 3 is a transverse cross section showing another example of a balancing means.

In addition to said weight 10, a wire drum 11 as shown in FIG. 3 may be used for a balancing means.

One end of a spiral spring 12 is mounted on the inside of said wire drum 11 while the other end of said spiral spring 12 is mounted on a rotation axis 13 of said wire drum 11. Spring force acts on said spiral spring 12 so as to wind said wire 9 when the wire 9 is pulled out, the end of which is fixedly mounted on the wire drum 11. The wire drum 11 is provided with a ratchet wheel 14 for stopping said wire drum 11 at optional positions. Said ratchet wheel 14 is stopped by means of click 15. A control lever 16 of said click 15 is installed in said main body 1 of a laser scalpel unit.

Accordingly, said wire 9 wound around said wire drum 11 is drawn out and simultaneously spring force is accumulated in said spiral spring 12, and the drum is fixed by means of said click 15, when said hand piece 7 is pulled. On the other hand, said wire 9 is wound around said wire drum 11 by the action of said spiral spring 12 by operating said control lever 16 to undo said click 15 from said ratchet wheel 14 and thereby said hand piece 7 is lifted.

As specifically described above on the basis of the preferred embodiment, according to the present invention, an optical fiber, which forms an optical wave guide of a laser scalpel, is provided with a hand piece at the forward end portion thereof, which facilitates the orientation of the forward end of the fiber toward the areas to be irradiated. Accordingly, the laser beam can be accurately directed to on the target areas to be irradiated in medical treatments and the range of operations can be extended. Furthermore, the optical fiber is not subjected to an excessive force which might break the fiber because a hand piece and the hanging down portion of the optical fiber are supported by a wire provided with a balancing means. Simultaneously, a laser scalpel of the present invention can be put out of the way when other medical treatments and operations are being performed, because the hand piece and hanging down portion of the fiber can be lifted and remain in the raised position.

What is claimed is:

1. A laser scalpel using an optical fiber for an optical wave guide said optical fiber being guided from a laser main body, housing a laser source therein, to areas to be irradiated by said laser scalpel, wherein:
   shore means provided on the laser main body for guiding said optical fiber, said optical fiber being provided with a hand piece on the exterior of one end thereof,
   said hand piece facilitating directing of the one end of said fiber toward the areas to be irradiated, and
   a supporting wire means, provided along said shore means, for permitting axial movement of itself along the lengthwise axis of said shore means, a forward end of said wire means being connected to said hand piece and a rear end of said wire means being connected to a balancing means for counterbalancing at least the weight of said hand piece.

2. The laser scalpel of claim 1, wherein said balancing means comprises a counter-balance weight.

3. The laser scalpel of claim 1, wherein said balancing means comprises a spring loaded wire drum.

4. The laser scalpel of claim 1, wherein:
   said shore means comprises an upright post standing on said laser main body and a horizontal arm fixed to said post at one end thereof, the one end of said fiber being hung down from another end of said arm which is not fixed to said post.

5. The laser scalpel of claim 4, wherein:
   said balancing means counter-balances the combined weight of said hand piece and the portion of said fiber which hangs down from said another end of said arm.

6. The laser scalpel of claim 1, wherein said hand piece is L-shaped.

7. A laser scalpel, comprising:
   a main laser body housing;
   a laser source mounted in said laser body housing;
   an optical fiber connected at one end, defined as its rear end, to said laser source;
   shore means, fixedly supported on said main body, for guiding said optical fiber so that its other end, defined as its forward end, is positioned for irradiating areas to be treated by said laser scalpel;
   a hand piece attached to said forward end of said optical fiber for facilitating the directing of said forward end;
   wire means, connected at one of its ends to said hand piece and supported along the length of said shore means for fully supporting said hand piece and for providing axial movement of wire included in said wire means along the axial length of said shore means; and
   balancing means connected to the other end of said wire means for fully counterbalancing at least the weight of said hand piece.

8. The laser scalpel of claim 7, wherein said balancing means comprises a counterbalance weight.

9. The laser scalpel of claim 7, wherein said balancing means comprises a spring loaded wire drum.

10. The laser scalpel of claim 7, wherein said shore means comprises an upright post standing at its lower end on said laser main body housing and a horizontal arm fixed at its one end to the upper end of said post, the forward portion of said fiber depending from the other end of said horizontal arm.

11. The laser scalpel of claim 10, wherein said balancing means counterbalances the combined weight of said hand piece and depending portion of said fiber.

12. The laser scalpel of claim 7, wherein said hand piece is L-shaped.

* * * * *